(12) United States Patent
Miller

(10) Patent No.: US 11,559,257 B2
(45) Date of Patent: Jan. 24, 2023

(54) CATHETER INSERT INCLUDING ONE OR MORE SENSORS

(71) Applicant: Covidien LP, Mansfield, MA (US)

(72) Inventor: David J. Miller, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 232 days.

(21) Appl. No.: 16/840,150

(22) Filed: Apr. 3, 2020

(65) Prior Publication Data
US 2021/0186427 A1    Jun. 24, 2021

Related U.S. Application Data

(60) Provisional application No. 62/952,776, filed on Dec. 23, 2019.

(51) Int. Cl.
*A61B 5/20* (2006.01)
*A61B 5/00* (2006.01)
(Continued)

(52) U.S. Cl.
CPC .............. *A61B 5/6852* (2013.01); *A61B 5/01* (2013.01); *A61B 5/036* (2013.01); *A61B 5/0538* (2013.01); *A61B 5/1032* (2013.01); *A61B 5/11* (2013.01); *A61B 5/14503* (2013.01); *A61B 5/14539* (2013.01); *A61B 5/14542* (2013.01); *A61B 5/14546* (2013.01); *A61B 5/205* (2013.01); *A61B 5/208* (2013.01); *A61B 5/6858* (2013.01); *A61L 29/041* (2013.01); *A61L 29/085* (2013.01); *A61L 29/14* (2013.01); *A61B 5/14507* (2013.01); *A61B 5/6853* (2013.01);
(Continued)

(58) Field of Classification Search
CPC ............ A61B 5/20; A61B 5/201; A61B 5/202
See application file for complete search history.

(56) References Cited

U.S. PATENT DOCUMENTS

| 1,870,942 A | 8/1932 | Beatty |
| 5,389,217 A | 2/1995 | Singer |

(Continued)

FOREIGN PATENT DOCUMENTS

| WO | 2002/096286 A1 | 12/2002 |
| WO | 2014/043650 A2 | 3/2014 |

(Continued)

OTHER PUBLICATIONS

"Clarity RMS", Renal Sense, retrieved from https://www.renalsense.com/clarity-rms/, retrieved on Feb. 4, 2020, 6 pp.
(Continued)

*Primary Examiner* — Michael J D'Abreu
(74) *Attorney, Agent, or Firm* — Shumaker & Sieffert, P.A.

(57) ABSTRACT

In some examples, a device includes a catheter insert elongated body defining a body lumen, the catheter insert elongated body being configured to be at least partially inserted to a catheter lumen defined by a catheter without covering a first fluid opening of the catheter and to form a fluidically tight coupling with the catheter, and one or more sensors positioned on the elongated body. At least one of the one or more sensors are configured to sense a substance of interest. The catheter insert elongated body includes a material that is a substantially non-permeable to the substance of interest.

21 Claims, 7 Drawing Sheets

(51) Int. Cl.

| | |
|---|---|
| *A61B 5/03* | (2006.01) |
| *A61B 5/145* | (2006.01) |
| *A61B 5/0538* | (2021.01) |
| *A61B 5/11* | (2006.01) |
| *A61L 29/04* | (2006.01) |
| *A61L 29/14* | (2006.01) |
| *A61B 5/103* | (2006.01) |
| *A61B 5/01* | (2006.01) |
| *A61L 29/08* | (2006.01) |
| *A61M 25/00* | (2006.01) |
| *A61M 25/01* | (2006.01) |

(52) U.S. Cl.
CPC ...... *A61B 2562/06* (2013.01); *A61M 25/0017* (2013.01); *A61M 25/0147* (2013.01); *A61M 2025/0004* (2013.01)

(56) References Cited

U.S. PATENT DOCUMENTS

| | | | |
|---|---|---|---|
| 6,238,339 | B1 | 5/2001 | Fiddian-Greene et al. |
| 6,602,243 | B2 | 8/2003 | Noda |
| 9,655,555 | B2 | 5/2017 | Burnett et al. |
| 9,662,058 | B2 | 5/2017 | Burnett et al. |
| 10,349,873 | B2 | 7/2019 | Kamath et al. |
| 10,391,275 | B2 | 8/2019 | Burnett et al. |
| 10,542,923 | B2 | 1/2020 | Chang et al. |
| 2006/0178571 | A1 | 8/2006 | Barnett |
| 2009/0105799 | A1 | 4/2009 | Hekmat et al. |
| 2013/0066166 | A1 | 3/2013 | Burnett et al. |
| 2016/0310711 | A1 | 10/2016 | Luxon et al. |
| 2017/0136209 | A1 | 5/2017 | Burnett et al. |
| 2019/0069831 | A1 | 3/2019 | Kuck et al. |
| 2019/0126006 | A1 | 5/2019 | Rehm et al. |
| 2019/0150801 | A1 | 5/2019 | Suehara et al. |
| 2019/0321588 | A1 | 10/2019 | Burnett et al. |
| 2019/0343445 | A1 | 11/2019 | Burnett et al. |
| 2020/0022636 | A1* | 1/2020 | Suehara ............... A61B 5/6852 |

FOREIGN PATENT DOCUMENTS

| | | |
|---|---|---|
| WO | 2014/210453 A2 | 12/2014 |
| WO | 2019/038732 A1 | 2/2019 |
| WO | 2019115809 A1 | 6/2019 |

OTHER PUBLICATIONS

Avulova et al., "Do Foley Catheters Adequately Drain the Bladder? Evidence from CT Imaging Studies", International Brazilian Journal of Urology, May 2015, vol. 41(3), pp. 552-555.

Parker, "Urinary Catheter Management: Minimizing the Risk of Infection", British Journal of Nursing, Nursing and Residential Care, vol. 8. No. 9, Apr. 1999, 8 pp.

Zhang et al., "The Permeability Characteristics of Silicone Rubber", Society for the Advancement of Material and Process Engineering, Coatings and Sealants Section, Nov. 6-9, 2006, 10 pp.

"Standard Performance Specification for Foley Catheter", ASTM International, Designation: F623—Mar. 19, 2019, 10 pp.

International Search Report and Written Opinion of International Application No. PCT/US2020/065365, dated Mar. 10, 2021, 16 pp.

U.S. Appl. No. 16/854,592, by Medtronic (Inventor: Miller), filed Apr. 21, 2020.

Office Action from U.S. Appl. No. 16/854,592 dated Aug. 26, 2022, 13 pp.

International Preliminary Report on Patentability from International Application No. PCT/US2020/065365, dated Jul. 7, 2022, 10 pp.

Response to Office Action dated Aug. 26, 2022 from U.S. Appl. No. 16/854,592, filed Nov. 2, 2022, 10 pp.

Notice of Allowance from U.S. Appl. No. 16/854,592 dated Nov. 21, 2022, 9 pp.

* cited by examiner

CATHETER INSERT INCLUDING ONE OR MORE SENSORS

This application claims the benefit of U.S. Provisional Patent Application 62/952,776, filed Dec. 23, 2019, the entire content of which is incorporated herein by reference.

TECHNICAL FIELD

This disclosure relates to medical devices, more particularly, to catheters.

BACKGROUND

Medical devices, such as catheters, may be used to assist a patient in voiding their bladder. In some instances, such catheters may be used during and/or after surgery. In the case of using a catheter to assist a patient in voiding their bladder, a Foley catheter is a type of catheter that may be used for longer time periods than a non-Foley catheter. Some Foley catheters are constructed of silicone rubber and include an anchoring member, which may be an inflatable balloon, that may be inflated in a patient's bladder to serve as an anchor so a proximal end of the catheter does not slip out of the patient's bladder.

SUMMARY

In general, the disclosure describes a medical device, such as an insert for a catheter (e.g., a Foley catheter). The medical device includes an elongated body configured to be at least partially inserted into a lumen of a catheter and one or more sensors positioned on the elongated body. In some examples, the medical device is configured to be inserted into the drainage lumen of a Foley catheter such that the proximal end of the medical device is close to, but does not cover the eyelet(s), drainage opening, or other entry way of urine from a patient's bladder into the drainage lumen of the catheter, allowing urine to flow from the patient's bladder into the Foley catheter and through the medical device. In some example, the medical device is configured to be inserted into the drainage lumen of a Foley catheter such that the distal end is external to the drainage lumen of the Foley catheter. In some examples, the distal end of the medical device may form a funnel or include a connector for connecting to a fluid collection container, such as a urine bag, with the funnel or connector being configured to prevent the medical device from being inserted so far into the drainage lumen of a Foley catheter that the proximal end of the medical device would cover the eyelet(s), drainage opening, or other entry way of urine from the patient's bladder into the drainage lumen of the Foley catheter.

In some examples, at least one of the one or more sensors may be placed on a distal portion of the medical device. As used herein, distal is used as defined in Section 3.1.4 of ASTM F623-19, Standard Performance Specification for Foley Catheter. That is, the proximal end of the medical device is the end closest to the patient. The distal end is therefore the end furthest from the patient. The one or more sensors located at the distal portion may be configured to sense one or more substances of interest, and a portion or an entirety of the elongated body of the medical device may comprise a material that is substantially non-permeable (e.g., non-permeable or nearly non-permeable) to the substances of interest to help minimize loss and/or contamination of the substances of interest as the fluid in which the substances of interest are present propagates through a lumen of the elongated body of the medical device to the one or more sensors located at the distal portion. In this way, the medical device is configured to enable a sensor to sense the substance of interest despite being positioned relatively far away from the fluid source, such as a bladder. As used herein, "sense" may include "detect" and/or "measure."

In one example, this disclosure is directed to a device including an elongated body defining a body lumen, the elongated body being configured to be at least partially proximally inserted into a catheter lumen defined by a catheter without covering a proximal fluid opening of the catheter and to form a fluidically tight coupling with the catheter, and one or more sensors positioned on the elongated body, at least one sensor of the one or more sensors configured to sense a substance of interest of a fluid within the body lumen, wherein the elongated body comprises a material that is a substantially non-permeable to the substance of interest.

In another example, this disclosure is directed to an assembly including a Foley catheter comprising a catheter elongated body defining a drainage lumen, the catheter elongated body comprising a catheter distal portion and a catheter proximal portion, the catheter proximal portion defining a first drainage opening fluidically coupled to the drainage lumen and the catheter distal portion defining a second drainage opening fluidically coupled to the drainage lumen; and a catheter insert comprising a catheter insert elongated body defining a body lumen, the catheter insert elongated body comprising a first body distal portion, a second body distal portion and a body proximal portion, the body proximal portion defining a first body fluid opening fluidically coupled to the body lumen and the first body distal portion defining a second body fluid opening fluidically coupled to the body lumen, wherein the catheter insert elongated body is configured such that when the first body distal portion is connected to the Foley catheter while the second body distal portion and the body proximal portion are inserted in the drainage lumen, a proximal end of the catheter insert elongated body remains distal to the first drainage opening of the Foley catheter; and one or more sensors positioned on the catheter insert elongated body, at least one of the one or more sensors configured to sense a substance of interest, wherein the catheter insert elongated body comprises a material that is a substantially non-permeable to the substance of interest, the material extending from the first body fluid opening to the at least one of the one or more sensors.

In another example, this disclosure is directed to a method including introducing a proximal end of a catheter insert into a lumen of a catheter, the catheter insert comprising an elongated body defining a body lumen and one or more sensors positioned on the elongated body, at least one sensor of the one or more sensors configured to sense a substance of interest of a fluid within the body lumen, wherein the elongated body comprises a material that is a substantially non-permeable to the substance of interest; proximally advancing the catheter insert into the drainage lumen so that a proximal end of the catheter insert is proximal to an anchoring member of the catheter and distal to a proximal fluid opening of the catheter; and fluidically coupling the catheter insert and the catheter.

The details of one or more examples are set forth in the accompanying drawings and the description below. Other features, objects, and advantages will be apparent from the description and drawings, and from the claims.

DETAILED DESCRIPTION

Figure 1:
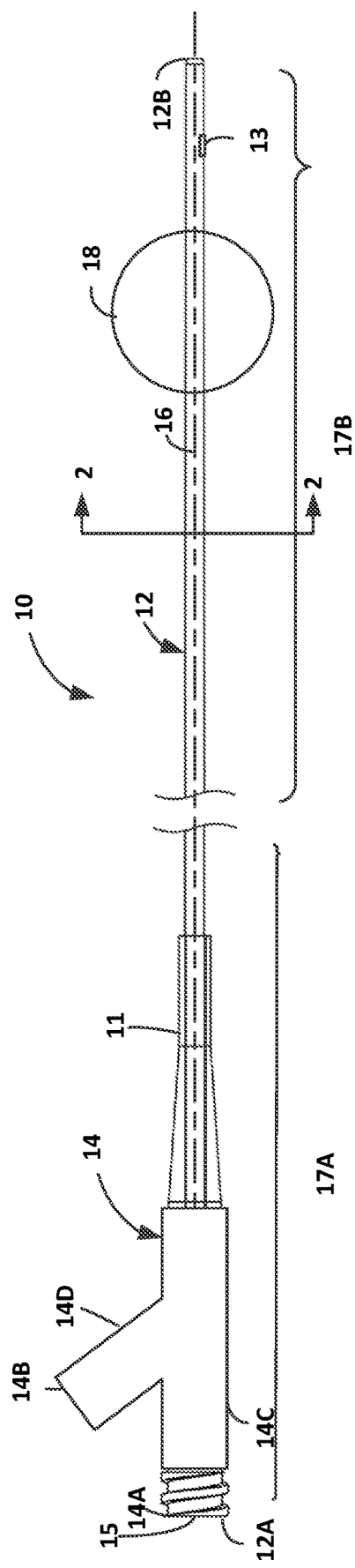
FIG. 1 is a diagram illustrating an example Foley catheter.

Acute kidney injury (AKI) is a complication that may occur after some medical procedures, such as some cardiac surgeries, e.g., coronary artery bypass grafting (CABG). AKI may also occur after other surgeries that are lengthy and involve significant blood loss or fluid shifts. For example, a surgery patient's body may alter where their blood is directed which may lead to hypoxia of a kidney. A cause of surgery-associated AKI is hypoxia of the kidneys, which may cause an inflammatory response in a kidney of the patient. This inflammatory response may cause degradation of renal function of the patient. The degradation of renal function may cause an accumulation of waste products in the bloodstream, which may delay the patient's recovery from the surgery and lead to more extended hospital stays and may even lead to further complications.

While systemic vital signs like cardiac output, blood pressure, and hematocrit may be useful for monitoring the kidney function of a patient, it may also be useful to monitor the oxygenation status of the kidneys in order to limit or even prevent the risk of AKI. Accurate monitoring of the oxygenation status of the kidneys can be challenging due to the inaccessibility of the kidneys. Near-Infrared spectroscopy (NIRS) measures regional oximetry, and has some utility in babies and relatively slender adults in measuring oxygenation of the kidneys, but may not have the depth of penetration and specificity required for some patients.

The present disclosure describes example medical devices that are configured to monitor kidney function of patients, such as patients who are undergoing or who have undergone surgeries, which may help reduce occurrences of AKI. The medical device includes at least one sensor configured to sense a parameter of a fluid of interest, such as urine in the case of kidney function monitoring. While urine, bladders, and AKI are primarily referred to herein to describe the example medical devices, in other examples, the medical devices may be used with other target locations in a patient, such as intravascular locations, and to monitor fluids of interest other than urine and/or other patient conditions other than kidney function. As discussed in further detail below, in some examples, an example medical device includes an oxygen sensor configured to sense an amount of oxygen dissolved in the urine (e.g., oxygen tension or uPO2 or PuO2) in the bladder and/or sense urine output (e.g., rate of urine production), from which a clinician or a device may be able to determine oxygenation status of the one or more kidneys of the patient.

Example parameters of interest sensed by a sensor described herein include, but are not limited to, any one or more of an amount of dissolved oxygen, urine concentration, urine electrical conductivity, urine specific gravity, urine biomarkers, amount of dissolved carbon dioxide in the urine, urine pH, bladder or abdominal pressure, bladder temperature, urine color, urine creatinine, or motion from an accelerometer or other motion sensor. In some cases, it may be desirable to sense one or more of these parameters relatively close to the kidneys as possible because when sensors are positioned further away from the kidneys, the risk of introducing noise or losing signal strength increases and/or the risk of the concentration or integrity of a substance of interest in the fluid of interest changing prior to being sensed by the sensor may increase. For example, an electrical, optical or radio frequency signal representative of a parameter sensed close to the kidneys, may be affected by noise and/or loss of signal strength as the signal travels from a sensor close to the kidneys to a device that may process the signal and display information regarding the sensed parameter. For example, in the case of a Foley catheter, it may be desirable to sense one or more of these parameters at the proximal end of the Foley catheter (e.g., in the bladder of the patient). However, placing these sensors at the proximal end of the catheter may increase the size and stiffness of the catheter and, as a result, may undermine the patient comfort or deliverability of the catheter. By design, a Foley catheter is made to be small and flexible, such that it can be inserted through the urethra and into the bladder of a patient. If a Foley catheter were stiffer, then it may be more difficult to comfortably insert the catheter into the bladder of the patient.

The amount of dissolved oxygen in a patient's urine may be indicative of kidney function or kidney health. For example, dissolved oxygen in a patient's urine in the bladder may correlate to perfusion and/or oxygenation of the kidneys, which is indicative of kidney performance. However, dissolved oxygen can be relatively difficult to measure. One way to measure dissolved oxygen is by fluorescence or luminescence lifetime sensor(s). The decay of glow is indicative of the level of oxygen in a patient's urine. To accurately measure the level of oxygen in a patient's urine, it may be desirable to take the measurement prior to any significant modification in the oxygen content in the urine, e.g., as close to the kidneys as possible. However, it may not be feasible to place a dissolve oxygen sensor at the proximal end of the catheter as doing so may increase cost, size, and flexibility of the catheter.

In accordance with examples of this disclosure, rather than integrating desired sensors in the proximal portion of a catheter (e.g., the portion that is to be inserted into the bladder of the patient or otherwise introduced in a patient), or positioning one or more sensors in the distal portion of the catheter, one or more sensors may be positioned at a distal portion of an elongated body of a medical device configured to be inserted in the catheter or distal to the distal end of the elongated body. The medical device may be referred to as a catheter insert. To help minimize or even eliminate degradation and/or contamination of a substance of interest in the fluid of interest (e.g., urine) before the fluid reaches a sensor at a distal portion of the medical device elongated body or distal to the distal end of the medical device elongated body, a portion or an entirety of the elongated body of the medical device comprises a material that is substantially non-permeable (e.g., non-permeable or nearly non-permeable) to the substances of interest. The medical device described herein may also be referred to as a catheter insert. While described herein as a catheter insert, in some examples, the medical device may be used with other devices or on a stand-alone basis.

In contrast to existing Foley catheters or other medical devices that are permeable to many substances of interest, the medical devices, such as the catheter inserts described herein, enable a sensor to relatively accurately sense a substance of interest in a fluid despite being positioned relatively far away from the fluid source, such as a bladder.

For example, some Foley catheters may include an elongated body made from silicone rubber, which is very porous to oxygen. Thus, using a dissolved oxygen sensor on the distal portion of such a Foley catheter to measure oxygen content in urine may result in erroneous or skewed measurements as the oxygen may dissipate from the urine through the walls of the Foley catheter as the urine travels from the bladder through a drainage lumen at the proximal portion of the catheter to the sensor on the distal portion of the catheter and into a surrounding environment. Oxygen may also permeate the urine through the walls of the Foley catheter as the urine travels from the bladder through the drainage lumen at the proximal portion of the catheter to the sensor on the distal portion of the catheter from the surrounding environment. For example, the oxygen may dissipate into or permeate from other tissues in the urinary tract and the atmosphere outside of the urinary tract. In some examples described herein, however, the medical device elongated body, configured to be at least partially inserted into the drainage lumen of a Foley catheter, comprises a material that is substantially non-permeable to oxygen, such that the amount of oxygen that dissipates or permeates through the walls of the medical device and through the walls of the Foley catheter having the medical device inserted is reduced relative to an elongated body of a standard Foley that is formed from silicone rubber.

In some examples, the catheter inserts described herein may be made entirely of a material that is substantially non-permeable to a substance of interest. In other examples, the catheter insert may be made of a plurality of materials, at least one of which is substantially non-permeable to a substance of interest. In some examples, the catheter inserts may maintain flexibility and are configured to minimize the degradation of signals of interest, but may maintain enough rigidity to be able to be inserted into a Foley catheter. Due to the material which is substantially non-permeable to a substance of interest, the catheter inserts may be stiffer than a standard Foley catheter. Thus, according to the techniques of this disclosure, a standard Foley catheter, which is relatively flexible by design, may be inserted into a patient's bladder and the catheter insert including the one or more sensors may be introduced into the drainage lumen of the Foley catheter, enabling the sensing of a substance of interest relatively far from the bladder without increasing the stiffness of the Foley catheter. By locating sensors at the distal portion of the elongated body of the catheter insert (or distal to a distal end of the elongated body), the sensors may be larger, may rely upon relatively more electrical and/or optical connections and the catheter itself may be smaller and more flexible than it would have been had the sensors been positioned at the proximal portion of the catheter.

The catheter insert is configured to be removed from the Foley catheter without requiring the Foley catheter to be removed from a patient. Accordingly, the catheter insert may be introduced into the drainage lumen of the Foley catheter as needed or desired. For example, if a Foley catheter is already being used on a patient and a clinician decides that sensing of a substance of interest of the patient is desirable, then the clinician may introduce the catheter insert into the already in use (in place in the bladder of the patient) Foley catheter, rather than removing the Foley catheter and inserting a sensing Foley catheter avoiding additional discomfort for the patient.

The catheter inserts may be formed of any suitable materials, which may be selected based on the substance of interest. For example, in some examples, at least one of the materials from which a catheter insert is formed may be a material that is substantially non-permeable to substances of interest, such as oxygen and carbon dioxide. "Substantially non-permeable" may refer to being non-permeable or non-permeable to the extent permitted by manufacturing tolerances, and/or having a permeability such that a percentage of loss and/or increase of the substance of interest through the material (e.g., through walls of an elongated body including the material) is relatively minimal (e.g., less than or equal to 5% at a flow rate of 10 ml/hour). In some examples, the material that is substantially non-permeable to substances of interest extends along the entire length and perimeter of the elongated body of the catheter insert. In other examples, the material that is substantially non-permeable to substances of interest extends along only part of the length and/or only part of the inner and/or outer perimeter of the elongated body, such as only between the proximal portion of the elongated body and the distal sensor location. By constructing the catheter insert using at least one material which is substantially non-permeable to substance of interest, sensors may be positioned at the distal portion of the catheter insert while providing more accurate sensor measurements while using a standard Foley catheter.

Any suitable materials may be used for the material that is substantially non-permeable to substances of interest, and the material can be selected based on the substance of interest. In "The Permeability Characteristics of Silicone Rubber," Haibing Zhang, Ph.D. and Andy Cloud, Society for the Advancement of Material and Process Engineering, 2006, Dr. Zhang presents a table of describing the oxygen permeability of different materials. The oxygen permeability of dimethylsilicone rubber is indicated as $60*10^9$ in $cm^3*cm/(s*cm^2*cmHg)$, nylon 6 is indicated as $0.004*10^9$, polyethylene terephthalate (PET) is indicated as $0.0019*10^9$, and polytetrafluoroethylene (PTFE) is indicated as $0.0004*10^9$. The permeability of dimethylsilicone rubber to carbon dioxide is indicated as 323. Thus, silicone rubber tends to be porous to substances of interest in monitoring kidney function, while nylon 6, PET and PTFE tend to be substantially non-permeable to substances of interest in monitoring kidney function. Foley catheters are typically constructed of latex or silicone rubber as the flexibility, elasticity, balloon-capability and low cost of latex and silicone rubber make latex and silicone rubber attractive materials.

In one example, according to the techniques of this disclosure, a catheter insert, such as a catheter insert configured to be inserted into a catheter, such as a Foley catheter, may be constructed of at least one material that is substantially non-permeable to a substance of interest, such as, but not limited to carbon dioxide or oxygen. In some examples, the catheter insert may be made solely of a material that is substantially non-permeable to a substance of interest, such as nylon, PET or PTFE in some examples in which the substance of interest is oxygen. In other examples, the catheter insert may be made partially of a material that is substantially non-permeable to a substance of interest. For example, the catheter insert may be made with a relatively thin layer of a substantially non-permeable material to the substance of interest disposed on another body material. By constructing a catheter insert, such as a catheter insert configured to be inserted into a Foley catheter, of at least one material that is substantially non-permeable to a substance of interest, degradation of the substance of interest during transit through the catheter insert and the Foley catheter may be mitigated or introduction of contaminants into the fluid in the catheter insert may be mitigated while using a standard Foley catheter. In one example, the relatively thin layer of substantially non-permeable material may be placed on the inner surface of a lumen defined by the catheter insert and through which a fluid of interest flows from a proximal portion of the catheter insert to a distal portion. In another example, in addition to or instead of the inner surface of the lumen, the relatively thin layer of the substantially non-permeable material may be placed on the outer surface of the catheter insert.

Certain parameters of urine or other fluids of interest are better measured at the proximal portion of a catheter, such as temperature and pressure. Measuring temperature at the distal portion may lead to relatively inaccurate measurements as the urine may experience heat exchange with the lumen, surrounding tissue and atmosphere while traveling from the proximal portion to the distal portion of the catheter insert. Measuring pressure at the distal portion may also lead to inaccurate measurements as the distal portion may be higher or lower than the abdomen. By measuring temperature and/or pressure at the proximal portion, these issues may be mitigated. In some examples, the catheter insert may have one or more sensors located at a proximal portion.

Thus, it may be desirable to have a catheter insert, such as a catheter insert configured to be inserted into a Foley catheter, having one or more sensors at one or more of a proximal portion or a distal portion and comprise a material that is substantially non-permeable to a substance of interest. In some examples, the catheter insert may include such sensors. In some examples, the catheter insert may be configured to attach sensors thereto. In some examples, the material is substantially non-permeable to oxygen and/or carbon dioxide. Sensors that may be positioned at the proximal portion may include a temperature sensor and/or a pressure sensor. Sensors that may be positioned at a distal portion may include sensors that sense urine output (e.g., flow or volume), urine concentration, amount of dissolved oxygen in the urine (oxygen tension or uPO2), amount of dissolved carbon dioxide in the urine, urine pH, urine color, urine creatinine, and/or motion.

FIG. 1 is a conceptual side elevation view of an example Foley catheter 10, which includes catheter elongated body 12, hub 14, and anchoring member 18. Foley catheter 10 includes a catheter distal portion 17A and a catheter proximal portion 17B. Catheter distal portion 17A includes a distal end 12A of Foley catheter 10 and is intended to be external to a patient's body when in use, while catheter proximal portion 17B includes a proximal end 12B of Foley catheter 10 and is intended to be internal to a patient's body when in use. For example, when catheter proximal portion 17B is positioned within a patient, e.g., such that proximal end 12B of Foley catheter 10 is within the patient's urethra and bladder, catheter distal portion 17A may remain outside of the body of the patient.

Catheter elongated body 12 is a structure (e.g., a tubular structure) that extends from hub 14 to proximal end 12B and defines one or more inner lumens. In the example shown in FIGS. 1, 2, 4A, and 4B, catheter elongated body 12 defines lumen 34 and lumen 36 (shown in FIGS. 4A-4C). In some examples, lumen 34 may be a drainage lumen for draining a fluid from a target site, such as a bladder. In other examples lumen 34 may be used for any other suitable purpose, such as to deliver a substance or another catheter insert to a target site within a patient. Lumen 34 may extend from proximal fluid opening 13 defined by catheter proximal portion 17B of elongated body 12 to distal fluid opening 14A at a distal end of Foley catheter 10, e.g., defined by hub 14. Both proximal fluid opening 13 and distal fluid opening 14A may be fluidically coupled to lumen 34, such that a fluid may flow from one of proximal fluid opening 13 or distal fluid opening 14A to the other of proximal fluid opening 13 or distal fluid opening 14A through lumen 34. In examples in which lumen 34 is a drainage lumen, proximal fluid opening 13 and distal fluid opening 14A may be drainage openings.

In some examples, catheter elongated body 12 has a suitable length for accessing the bladder of a patient through the urethra. The length may be measured along central longitudinal axis 16 of catheter elongated body 12. In some examples, catheter elongated body 12 may have an outer diameter of about 12 French to about 14 French, but other dimensions may be used in other examples. Catheter distal portion 17A and catheter proximal portion 17B may each have any suitable length.

In the example shown in FIG. 1, distal end 12A of catheter elongated body 12 is received within hub 14 and is mechanically connected to hub 14 via an adhesive, welding, or another suitable technique or combination of techniques.

Hub 14 is positioned at a distal end of catheter elongated body 12 and defines an opening(s) (e.g., 14A, 14B) through which the one or more inner lumens (e.g., lumen 34 shown in FIGS. 4A and 4B) of catheter elongated body 12 may be accessed and, in some examples, closed. While hub 14 is shown in FIG. 1 as having two arms, 14C and 14D, (e.g., a "Y-hub"), hub 14 may have any suitable number of arms, which may depend on the number of inner lumens defined by catheter elongated body 12. For example, each arm of hub 14 may be fluidically coupled to a respective inner lumen of catheter elongated body 12. In the example of FIG. 1, hub 14 comprises a distal fluid opening 14A, which is fluidically coupled to lumen 34, and an inflation opening 14B, which is fluidically coupled to an lumen 36 (shown in FIGS. 4A-4C) of catheter elongated body 12. In examples in which anchoring member 18 does not include an expandable balloon, rather than defining lumen 36, catheter elongated body 12 may define an inner lumen configured to receive a deployment mechanism (e.g., a pull wire or a push wire) for deploying an expandable structure anchoring member 18 and hub 14 may comprise distal fluid opening 14A and an opening 14B via which a clinician may access the deployment mechanism.

A fluid collection container (e.g., a urine bag) may be attached to distal fluid opening 14A for collecting urine draining from the patient's bladder. Inflation opening 14B may be operable to connect to an inflation device to inflate anchoring member 18 positioned on catheter proximal portion 17B of Foley catheter 10. Anchoring member 18 may be uninflated or undeployed when not in use. Hub 14 may include connectors, such as connector 15, for connecting to other devices, such as the fluid collection container and the inflation source. In some examples, connector 15 includes a luer-type connector, a threaded connection, or other connector configured to establish a fluid-tight seal with another device. In some examples, Foley catheter 10 includes strain relief member 11, which may be a part of hub 14 or may be separate from hub 14.

Catheter proximal portion 17B of Foley catheter 10 comprises anchoring member 18 and proximal fluid opening 13. Anchoring member 18 may include any suitable structure configured to expand from a relatively low profile state to an expanded state in which anchoring member 18 may engage with tissue of a patient (e.g., inside a bladder) to help secure and prevent movement of catheter proximal portion 17B out of the body of the patient. For example, anchoring member 18 may include an anchor balloon or other expandable structure. When inflated or deployed, anchoring member 18 may function to anchor Foley catheter 10 to the patient, for example, within the patient's bladder. In this manner, the portion of Foley catheter 10 on the proximal side of anchoring member 18 may not slip out of the patient's bladder. Proximal fluid opening 13 may be positioned on the surface of elongated body 12 between anchoring member 18 and the proximal end 12B (as shown) or may be positioned at proximal end 12B, thereby defining an opening at a proximal-most end of Foley catheter 10.

Catheter elongated body 12 may be structurally configured to be relatively flexible, pushable, and relatively kink- and buckle-resistant, so that it may resist buckling when a pushing force is applied to a relatively distal portion of the catheter insert to advance the elongated body proximally through the urethra and into the bladder. Kinking and/or buckling of catheter elongated body 12 may hinder a clinician's efforts to push the elongated body proximally.

In some examples, catheter elongated body 12 is formed from two or more discrete and separate longitudinally extending segments that are mechanically connected to each other, e.g., at axial butt joints. In other examples, catheter elongated body 12 may have a unibody construction (e.g., formed from one continuous piece of material, such as being extruded to define one seamless body) and may be substantially continuous along a length of catheter elongated body 12.

In some examples, at least a portion of an outer surface of catheter elongated body 12 includes one or more coatings, such as an anti-microbial coating, and/or a lubricating coating. The lubricating coating may be configured to reduce static friction and/kinetic friction between catheter elongated body 12 and tissue of the patient as catheter elongated body 12 is advanced through the urethra.

Figure 2:
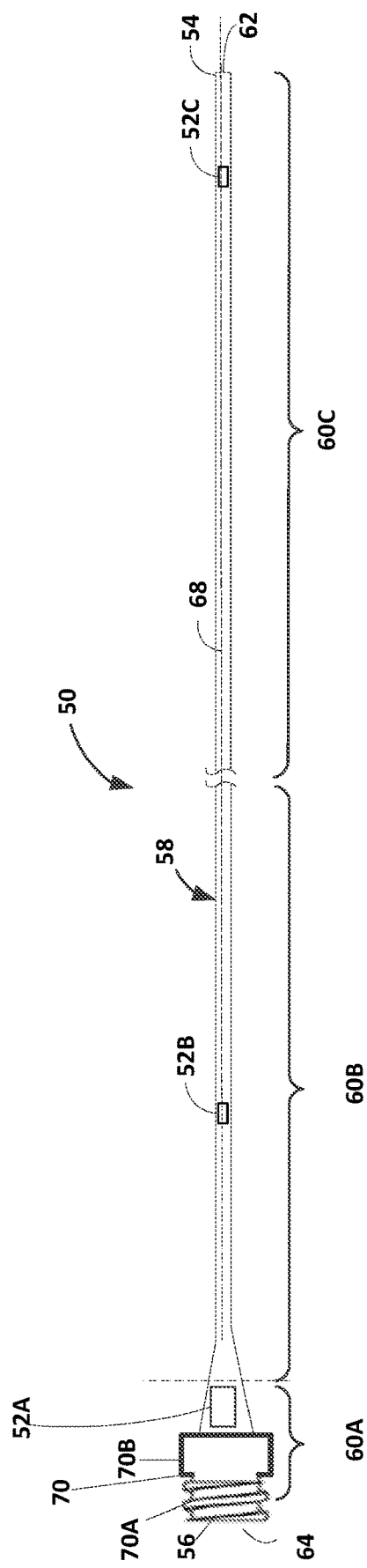
FIG. 2 is a diagram illustrating an example medical device configured to be inserted into a Foley catheter.

FIG. 2 is a conceptual side elevation view of an example catheter insert 50, which includes a catheter insert elongated body 58 and one of more sensors 52. While catheter insert 50 is primarily described herein as being used with a Foley catheter, in other examples, catheter insert 50 may be used with other catheters or for other purposes, such as to drain wounds or for intravascular monitoring or medical procedures. In addition, in some examples, catheter insert 50 is configured to be used without being introduced into a catheter, such as by being directly introduced into a patient to sense one or more parameters discussed herein.

Catheter insert elongated body 58 includes a first body distal portion 60A and second body distal portion 60B and a body proximal portion 60C. Second body distal portion 60B and body proximal portion 60C may be configured to be insertable into and/or removable from a lumen of another catheter insert, such as Foley catheter 10. In some examples, first body distal portion 60A is configured to remain external to lumen 34 of Foley catheter 10 when second body distal portion 60B and body proximal portion 60C are inserted into the drainage lumen of Foley catheter 10. First body distal portion 60A includes a body distal end 64 of catheter insert elongated body 58. In some examples, first body distal portion 60A is configured to facilitate the ingress or egress of fluid from a lumen defined by catheter insert elongated body 58. For example, first body distal portion 60A can include connector 70, e.g., at a distal-most end of catheter insert 50, that is configured to define a fluid tight seal with Foley catheter 10 to help prevent fluid from lumen 34 of Foley catheter 10 from flowing out of lumen 34 between any spaced defined between catheter insert 50 and Foley catheter 10 when catheter insert 50 is introduced within lumen 34.

In some examples, connector 70 may include a threaded male section 70A that is configured to fluidically connect to mating section on a device, such as a urine collection device.

Figure 3:
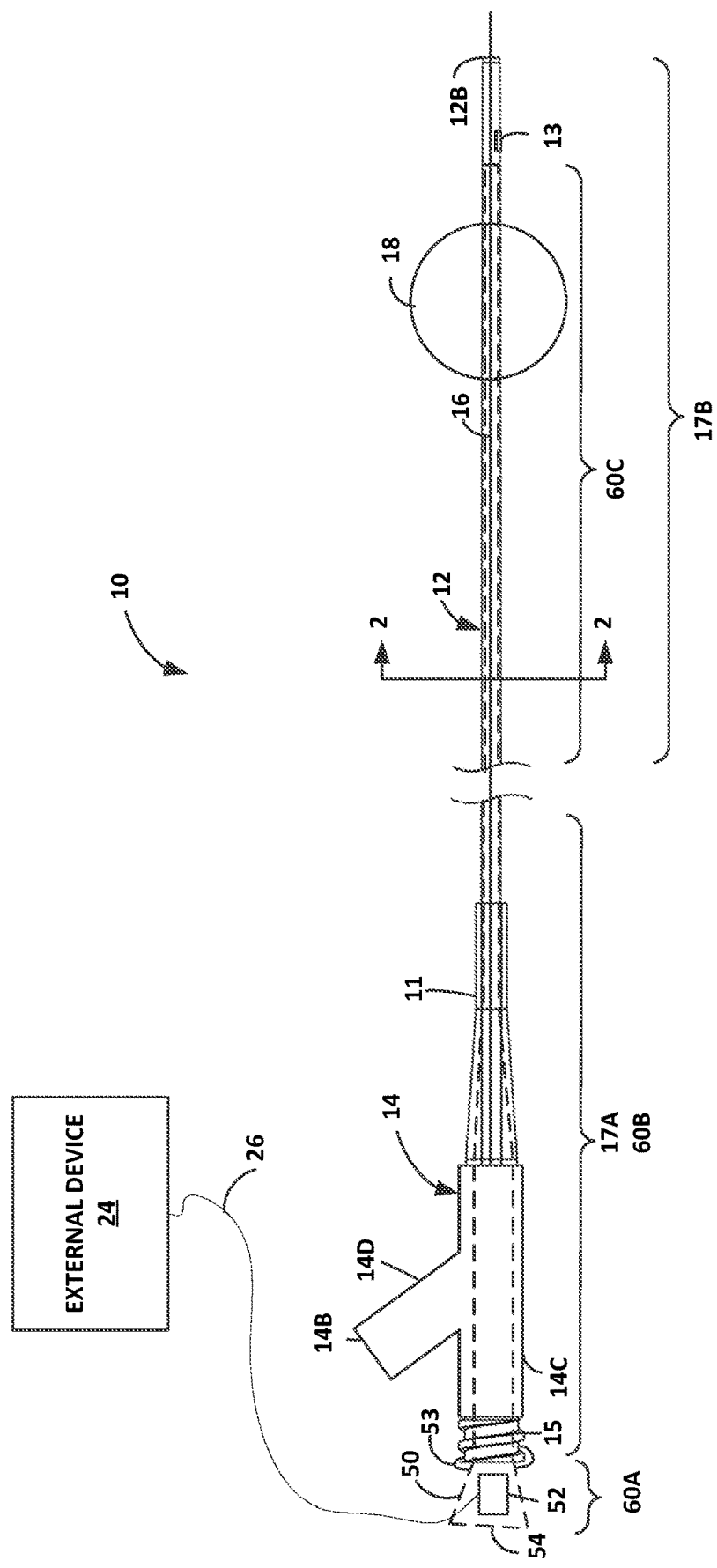
FIG. 3 is a diagram illustrating a Foley catheter having the example medical device of FIG. 2 inserted therein.

In some examples, connector 70 may is also configured to form a fluidically tight coupling with Foley catheter 10 such that when a fluid, such as urine, is flowing through catheter insert 50, which is inserted in lumen 34 of Foley catheter 10, the fluid does not leak at the distal end 12A of Foley catheter 10. For example, connector 70 may include a threaded female section 70B that is configured to thread onto connector 15 of Foley catheter 10 to form a fluidically tight coupling with Foley catheter 10. In some examples, other techniques are used to prevent leakage at the distal end of the Foley catheter. For example, first body distal portion 60A may include a press-fit funnel connector, such that when pushed into distal end 12A of Foley catheter 10 a compliant material (either on first body distal portion 60A, on distal end 12A or both) forms a fluidically tight coupling between first body distal portion 60A and distal end 12A of Foley catheter 10 (e.g., the compliant material may form a lip that is attached to the outside of connector 15, as shown in FIG. 3). As another example, a compressible, sealing material (e.g., formed at least in part from an expandable material such as a hydrogel, hydrophilic polymer, or the like) may be positioned an outer surface of connector 70 so that when catheter insert 50 is introduced into lumen 34 of Foley catheter 10 and is positioned such that connector 70 abuts distal end 12A of Foley catheter 10, the sealing member is at the interface (e.g., compressed) between connector 70 and Foley catheter 10. In some examples, the sealing member is configured to expand in the presence of fluid to fill any gaps at the interface between an outer surface of connector 70 and distal end 12A of Foley catheter 10 to form a fluid tight connection between Foley catheter 10 and catheter insert 50 or at least to lessen any leaks between Foley catheter 10 and catheter insert 50 at the distal end 12A of Foley catheter 10.

In some examples, first body distal portion 60A is configured to interact with hub 14 to help a clinician properly position catheter insert elongated body 58 within lumen 34 of Foley catheter. For example, connector 70 can be positioned along catheter insert 50 such that connector 70, e.g., due to having a maximum cross-sectional dimension larger than a cross-sectional dimension of lumen 34, prevents first body distal portion 60A from entering the lumen 34 of Foley catheter 10. In other examples, first body distal portion 60A may include a structural feature other than connector 70 configured to act as a stop to limit insertion of catheter insert 50 too far proximally into lumen 34 of Foley catheter 10, e.g., to prevent catheter insert elongated body 58 from blocking proximal fluid opening 13 of Foley catheter 10. For example, in addition to or instead of connector 70, first body distal portion 60A may contain a lip or tab or form a funnel to aid in preventing catheter insert 50 from being inserted too far proximally into lumen 34. Connector 70 or the other structure contacting hub 14 while second body distal portion 60B and body proximal portion 60C are positioned in lumen 34 may provide tactile feedback to a clinician that catheter insert 50 is properly aligned with Foley catheter 10, e.g., such that catheter insert elongated body 58 does not cover proximal fluid opening 13 in lumen 34 or that a fluidically tight coupling has been formed between catheter insert 50 and Foley catheter 10.

Second body distal portion 60B is intended to be internal to the drainage lumen of Foley catheter 10 but external to a patient's body when catheter insert 50 is inserted into Foley catheter 10. Body proximal portion 60C is intended to be internal to the drainage lumen of Foley catheter 10 and internal to a patient's body when catheter insert 50 is inserted into the drainage lumen of Foley catheter 10, such that body proximal portion 60C is within catheter proximal portion 17B.

Catheter insert elongated body 58 is a structure that extends from body distal end 64 to body proximal end 62 and defines one or more inner lumens. In the example shown in FIGS. 2-4C, catheter insert elongated body 58 defines body lumen 66 (shown in FIGS. 4B and 4C). In some examples, body lumen 66 may be a drainage lumen configured to drain a fluid from a target site, such as a bladder. In other examples, body lumen 66 may be used for any other suitable purpose, such as to deliver a substance or another medical device to a target site within a patient. Body lumen 66 may extend from first body fluid opening 54 to second body fluid opening 56. Both first body fluid opening 54 and second body fluid opening 56 may be fluidically coupled to body lumen 66, such that a fluid may flow from one of first body fluid opening 54 or second body fluid opening 56 to the other of first body fluid opening 54 or second body fluid opening 56 through body lumen 66. In the example where body lumen 66 is a drainage lumen, first body fluid opening 54 and second body fluid opening 56 may be drainage openings.

In some examples, catheter insert elongated body 58 has a suitable length for accessing the bladder of a patient through the urethra. For example, the combined length of second body distal potion 60B and body proximal portion 60C of catheter insert elongated body 58 may be of a length that when catheter insert 50 is fully inserted into Foley catheter 10 (e.g., connector 70 prevents further proximal advancement of catheter insert elongated body 58 into lumen 34 of Foley catheter 10), body proximal end 62 is distal to proximal fluid opening 13 of Foley catheter 10 and, in some examples, proximal to anchoring member 18. In this manner, catheter insert 50 does not block the flow of urine through proximal fluid opening 13, enabling the urine to flow into Foley catheter 10 and into catheter insert 50 through body fluid opening 54. The length may be measured along central longitudinal axis 68 of catheter insert elongated body 58. In some examples, catheter insert elongated body 58 may have an outer diameter of about 2 French to about 6 French, but other dimensions may be used in other examples such that second body distal portion 60B and body proximal portion 60C may be insertable into and/or removeable from another medical device, such as Foley catheter 10. In some examples, catheter insert elongated body may have an outer diameter that hinders or prevents urine from flowing between an outer surface of catheter insert 50 and inner lumen 34 of Foley catheter 10. First body distal portion 60A, second body distal portion 60B, and body proximal portion 60C of catheter insert elongated body 58 may each have any suitable length.

A fluid collection container (e.g., a urine bag) may be attached to second body fluid opening 56 for collecting urine draining from the patient's bladder. In some examples, first body distal portion 60A may include a connector, such as connector 70, for connecting to other devices, such as the fluid collection container. In some examples, first body distal portion 60A may define a funnel.

Catheter insert 50 includes one or more sensors, such as sensor 52A, 52B or 52C (collectively or individually one or more sensors 52), configured to sense a fluid or patient parameter indicative of kidney status of a patient. While shown as being located on first body distal portion 60A of catheter insert 50, in some examples one or more sensors 52 may be located on second body distal portion 60B, body proximal portion 60C or any combination of first body distal portion 60A, second body distal portion 60B, and/or body proximal portion 60C. In some examples, some parameters should be sensed relatively close to the fluid source, such as the bladder, because the parameters may substantially change as a function of time or based on the location at which the parameter is sensed. Temperature is one example parameter that may substantially change as a function of time and pressure is one example parameter that may change based on the location at which the parameter is sensed. Temperature and pressure are two parameters that may be better sensed at catheter proximal portion 17B of Foley catheter 10 (relatively close to the fluid source). Thus, in some examples one or more sensors 52 may be located at body proximal portion 60C of catheter insert 50, such as a temperature sensor and/or pressure sensor.

One or more sensors 52 are configured to communicate sensor data to external device 24 (FIG. 3) via an electrical, optical, wireless or other connection. In some examples in which one or more of sensors 52 are located on second body distal portion 60B or body proximal portion 60C, the one or more sensors may communicate sensor data to external device 24 through a connection(s) within catheter insert elongated body 58 of catheter insert 50 via embedded wire(s) or optical cable(s). In other examples, wire(s) or optical cable(s) may run between the outer surface of catheter insert 50 and lumen 34, within another inner lumen of a catheter, or outside of Foley catheter 10. In other examples, one or more sensors 52 may communicate sensor data to external device 24 via a wireless communication technique.

In some examples, the one or more sensors located on first body distal portion 60A (e.g., sensor 52A) or second body distal portion 60B (e.g., sensor 52B) may be sensors that are relatively larger, require relatively more electrical or optical connections, and/or that sense parameters that may be sensed relatively far away from the fluid source compared to the parameters sensed by sensors located on body proximal portion 60C. Thus, the parameters that one or more or one or more sensors 52 located on first body distal portion 60A or second body distal portion 60B are configured to sense may include parameters that do not substantially change as a function of time or based on the location at which the parameter is sensed. As the catheter insert of the present disclosure includes a material that is substantially non-permeable to a substance of interest, sensors located on first body distal portion 60A or second body distal portion 60B may also be configured to sense parameters that do otherwise substantially change as a function of time or based on the location at which the parameter is sensed, such as an amount of dissolved oxygen in the urine (oxygen tension or uPO2) or amount of dissolved carbon dioxide in the urine. In some examples, one or more sensors 52 may include sensors configured to sense urine output (e.g., flow or volume), urine concentration, amount of dissolved oxygen in the urine, amount of dissolved carbon dioxide in the urine, urine pH, urine color, urine creatinine, urine electrical conductivity, urine specific gravity, urine biomarkers, and/or motion. For example, one or more sensors 52 may include a color sensor, creatine sensor, flow sensor, ph sensor, volume sensor, dissolved gas sensor (such as a dissolved oxygen sensor or a dissolved carbon dioxide sensor) urine electrical conductivity sensor, urine specific gravity sensor, urine biomarkers sensor, or a motion sensor.

In some examples, one or more sensors 52 are mechanically connected to catheter insert elongated body 58 or another part of catheter insert 50 using any suitable technique, such as, but not limited to, an adhesive, welding, by being embedded in catheter insert elongated body 58, via a crimping band or another suitable attachment mechanism or combination of attachment mechanisms. In some examples, one or more sensors 52 are not mechanically connected to catheter insert elongated body 58 or catheter insert 50, but is instead mechanically connected to a structure that is distal to body distal end 64 of catheter insert 50, such as to tubing that extends between hub 14 and a fluid collection container.

FIG. 3 is a diagram illustrating catheter insert 50 inserted into Foley catheter 10. In the example of FIG. 3, catheter insert 50 is shown with dashed lines. For example, body proximal portion 60C of catheter insert 50 may be inserted through distal fluid opening 14A, e.g., a second drainage opening, (shown in FIG. 1) of Foley catheter 10 and into lumen 34 (shown in FIG. 4A) such that body proximal portion 60C of catheter insert 50 is received within catheter proximal portion 17B of Foley catheter 10 and second body distal portion 60B of catheter insert 50 is received within catheter distal portion 17A of Foley catheter 10. In this example, first body distal portion 60A of catheter insert 50 remains external to Foley catheter 10. In some examples, when connector 70 is in contact with distal end 12A of Foley catheter 10 or lip 53 (as defined by hub 14 in the example shown in FIG. 3), such that catheter insert elongated body 58 cannot be introduced any further into lumen 34 without removing connector 70 or otherwise undermining the integrity of connector 70, body proximal end 62 of catheter insert 50 is distal to proximal fluid opening 13, e.g., a first drainage opening, permitting fluid, such as urine to flow into Foley catheter 10 via proximal fluid opening 13, through first body fluid opening 54 of catheter insert 50, and through body lumen 66 of catheter insert 50 to fluid opening 56 of catheter insert 50. A fluid collection container, e.g., a urine bag, may be fluidly coupled to fluid opening 56 (FIG. 2).

In some examples, one or more sensors 52 may be external to Foley catheter 10 when catheter insert 50 is inserted into Foley catheter 10. In other examples, one or more of one or more sensors 52 may be internal to Foley catheter 10 when catheter insert 50 is inserted into Foley catheter 10. One or more sensors 52 may be coupled to external device 24.

One or more sensors 52 may be configured to communicate sensor data to an external device 24. External device 24 may be a computing device, such as a workstation, a desktop computer, a laptop computer, a smart phone, a tablet, a server or any other type of computing device that may be configured to receive, process and/or display sensor data. One or more sensors 52 may communicate sensor data to the external device via a connection 26. Connection 26 may be an electrical, optical, wireless or other connection.

Although only one sensor 52 is shown in FIG. 3, in other examples, catheter insert 50 can include any suitable number of sensors on body proximal portion 60C, any suitable number of sensors on second body distal portion 60B, and any suitable number of sensors on first body distal portion 60A, where the sensors on body proximal portion 60C sense the same or different parameters, the sensors on second body distal portion 60B sense the same or different parameters, and the sensors on first body distal portion 60A sense the same or different parameters. In addition, some or all of the sensors on body proximal portion 60C may sense the same or different parameters as the sensors on second body distal portion 60B, or the sensors on first body distal portion 60A. For example, in the case where sensors on the distal portion may be temperature dependent, it may be desirable to sense temperature on the body proximal portion 60C, second body distal portion 60B and/or first body distal portion 60A.

Catheter insert elongated body 58 may be structurally configured to be relatively flexible, pushable, and relatively kink- and buckle-resistant, so that it may resist buckling when a pushing force is applied to a relatively distal portion of catheter insert 50 to advance the elongated body proximally through distal fluid opening 14A of Foley catheter 10. Kinking and/or buckling of catheter insert elongated body 58 may hinder a clinician's efforts to push the elongated body proximally.

As some substances of interest may dissipate from or permeate into a fluid, such as urine, within lumen 34 of catheter elongated body 12 of Foley catheter 10, catheter insert elongated body 58 of catheter insert 50 may be constructed of or to include a material that is substantially non-permeable (e.g., non-permeable or nearly non-permeable) to one or more substances of interest. In some examples, catheter insert elongated body 58 may be entirely or principally constructed of a material that is substantially non-permeable to substances of interest. In other examples, catheter insert elongated body 58 may be constructed such that the material is positioned to minimize or even prevent the egress of the substance of interest out of body lumen 66 via a sidewall of catheter insert elongated body 58, where the sidewall may be the wall extending between body distal end 64 and body proximal end 62. In addition to or instead of minimizing or preventing the egress the substance of interest out of body lumen 66 via the sidewall, in some examples, the material may be configured and positioned to minimize or even prevent the ingress of the substance of interest or other contaminants in some examples into body lumen 66 via the sidewall.

Figure 4A:
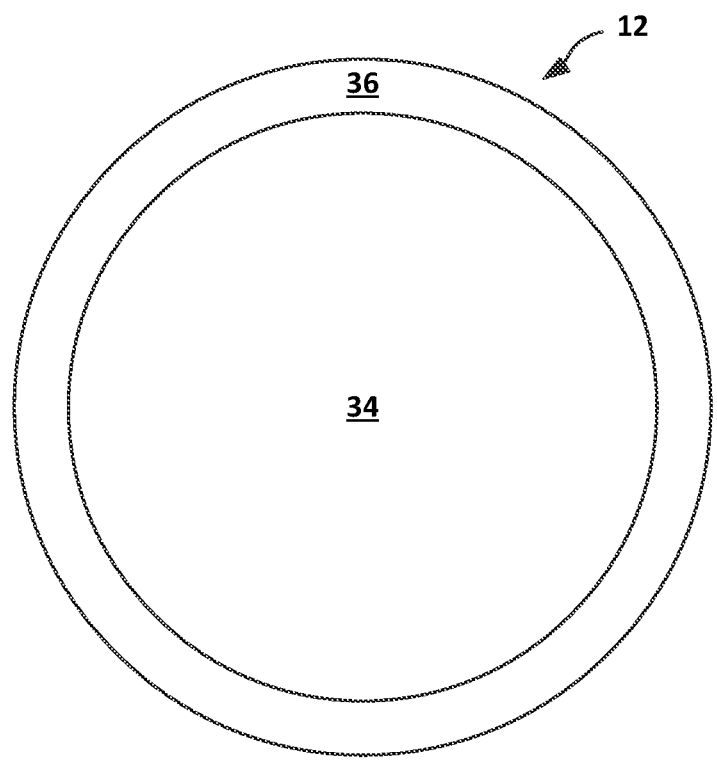
FIGS. 4A-4C are diagrams illustrating example cross-sectional views of the medical device of FIG. 3 and the Foley catheter while the medical device is inserted in the Foley catheter, the cross-section being taken along lines 2-2 of FIG. 3.
Figure 4B:
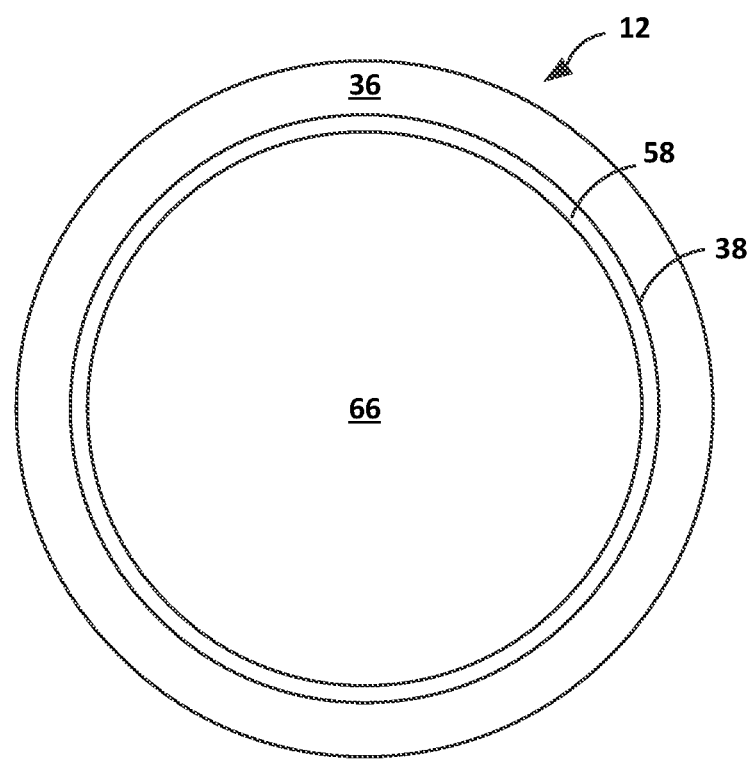

As discussed in further detail relative to FIGS. 4A and 4B, in some examples, a material that is substantially non-permeable to a substance of interest may be positioned along an inner surface of catheter insert elongated body 58 that defines body lumen 66. In addition to or instead of being on the inner surface, the material may be positioned along an outer surface of catheter insert elongated body 58. In this manner, the material that is substantially non-permeable to a substances of interest may to help minimize or even eliminate degradation and/or contamination of the substances of interest as the fluid in which the substances of interest are present propagates through body lumen 66 of catheter insert elongated body 58 to one or more sensors 52 that may be located on first body distal portion 60A or distal to first body distal portion 60A. In this way, catheter insert 50 is configured to enable one or more sensors 52 to sense the substance of interest even when one or more sensors 52 are positioned relatively far away from body proximal end 62 of catheter insert elongated body 58 and the fluid source, such as a bladder.

The material that is substantially non-permeable to a substance of interest may extend from any suitable position on the body proximal portion 60C of catheter insert elongated body 58 to any suitable position on the second body distal portion 60B or first body distal portion 60A of catheter insert elongated body 58 such that the degradation and/or contamination of substances of interest is inhibited. For example, the material may extend from body proximal end 62 to body distal end 64. In other examples, the material may extend from body proximal end 62 to one or more sensors 52.

In some examples, catheter insert elongated body 58 is formed from two or more discrete and separate longitudinally extending segments that are mechanically connected to each other, e.g., at axial butt joints. In other examples, rather than being formed from two or more discrete and separate longitudinally extending segments that are mechanically connected to each other, e.g., at axial butt joints, catheter insert elongated body 58 may be substantially continuous along a length of catheter insert elongated body 58. A substantially continuous catheter insert elongated body 58 may be better configured to distribute forces in a longitudinal direction (in a direction along central longitudinal axis 68) and rotational direction (rotation about central longitudinal axis 68) compared to an elongated body including two or more longitudinally extending segments that are mechanically connected to each other. Thus, the substantially continuous construction of catheter insert elongated body 58 may contribute to the ability of catheter insert elongated body 58 to transfer axial pushing forces from first body distal portion 60A of catheter insert elongated body 58 to body proximal portion 60C, as well transfer rotational forces (if any) applied from first body distal portion 60A of catheter insert elongated body 58 to body proximal portion 60C.

In some examples, at least a portion of an outer surface of catheter insert elongated body 58 includes one or more coatings, such as a lubricating coating. The lubricating coating may be configured to reduce static friction and/or kinetic friction between catheter insert elongated body 58 and lumen 34 of Foley catheter 10 as catheter insert elongated body 58 is advanced.

Figure 4C:
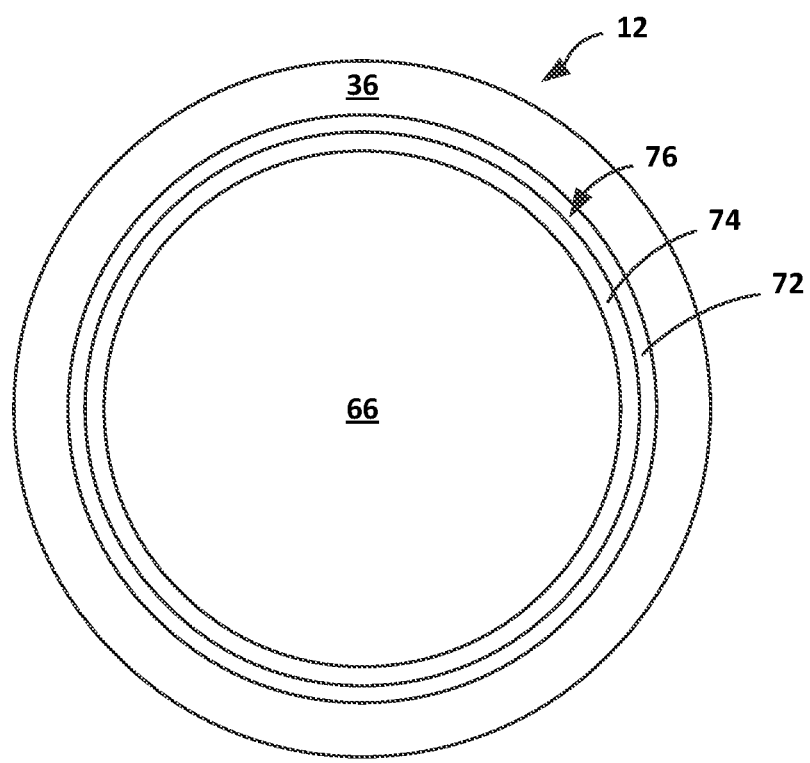

FIGS. 4A-4C are diagrams illustrating example cross-sections of catheter insert 50 and Foley catheter 10, where the cross-section is taken along line 2-2 in FIG. 3 in a direction orthogonal to central longitudinal axis 16. FIG. 4A depicts a cross section of catheter elongated body 12 of Foley catheter 10, which defines lumen 34 and lumen 36. In some examples, lumen 34 may be referred to as a drainage lumen and be configured to drain urine from a bladder of a patient, and lumen 36 may referred to as an inflation lumen in examples in which lumen 36 is configured to deliver an inflation fluid to anchoring member 18 (shown in FIG. 1). In operation, lumen 34 may serve as a passage for urine entering Foley catheter 10 through proximal fluid opening 13 to distal fluid opening 14A.

FIG. 4B is a diagram illustrating a cross-section of Foley catheter 10 and example catheter insert 50 when catheter insert 50 is inserted in Foley catheter 10. In the example of FIG. 4B, catheter insert 50 may be constructed of a material that is substantially non-permeable to a substance of interest, such as oxygen and/or carbon dioxide. In some examples, the material may be at least one of nylon, PET, or PTFE.

As depicted, an outer perimeter of catheter insert elongated body 58 contacts inner surface 38 defining lumen 34 of Foley catheter 10. In other examples, the outer perimeter of catheter insert elongated body 58 may not contact or may partially contact inner surface 38 defining lumen 34. In some examples, the outer perimeter of catheter insert elongated body 58 contacts or partially contacts inner surface 38 defining lumen 34 along the entire length of second body distal portion 60B and body proximal portion 60C. In other examples, the outer perimeter of catheter insert elongated body 58 does not contact or partially contact inner surface 38 defining lumen 34 along the entire length of second body distal portion 60B and body proximal portion 60C. Body lumen 66 of catheter insert 50 may serve as a passage for urine entering catheter insert 50 through first body fluid opening 54 to second body fluid opening 56. While body lumen 66 is depicted as circular in cross-section, it may be any shape in other examples.

FIG. 4C is a diagram illustrating a cross-section of Foley catheter 10 and another example catheter insert when a catheter insert is inserted in Foley catheter 10. The catheter insert of FIG. 4C may be an example of catheter insert 50. In the example shown in FIG. 4C, the catheter insert includes a catheter insert elongated body 76 made of a plurality of layers materials, for example layer of first material 74 and layer of second material 72, which can be arranged concentrically in examples in which catheter insert elongated body 76 has a circular cross-section or similarly stacked in a radially outward direction in examples in which catheter insert elongated body 76 defines a non-circular cross-section (e.g., oval, rectangular, square, and the like). In some examples, layer of first material 74 is relatively non-permeable to substances of interest, such as oxygen and/or carbon dioxide, and is positioned along an inner surface of catheter insert elongated body 76 that defines body lumen 66. In some examples, layer of second material is relatively permeable to substances of interest, such as oxygen and/or carbon dioxide. In some examples, layer of first material 74 extends along an entire length of body lumen 66, while in other examples, layer of first material 74 only extends along only a part of a length of body lumen 66, for example, from a body proximal portion to one or more sensors, which may help maintain a desired level of flexibility of catheter insert elongated body 76. In addition, as shown in FIG. 4C, in some examples, layer of first material 74 extends around an entire inner perimeter of body lumen 66 (e.g., an inner circumference in examples in which the inner perimeter is circular in cross-section).

Layer of first material 74 may be selected based on the one or more substances of interest for which it is desirable to limit outflow out of catheter insert elongated body 76 or inflow into catheter insert elongated body 76. In some examples, layer of first material 74 may be one or more of nylon, PET, or PTFE.

In some examples, the layer of first material 74 is relatively thin, where the thickness of layer of first material 74 is measured in a direction orthogonal to central longitudinal axis 16, e.g., in a radial direction. For example, layer of first material 74 may be in the range of 0.001 to 0.100 inches (0.0254 mm to 2.54 mm) thick. In other examples, the layer of first material 74 may be in the range of 0.0005 to 0.050 inches (0.0127 mm to 1.27 mm) thick. By keeping layer of first material 74 relatively thin, the catheter insert may remain relatively flexible.

In other examples, layer of first material 74 may relatively permeable to substances of interest, but layer of second material 72 may be relatively non-permeable to substances of interest. For example, layer of second material 72 may be, for example, an outermost surface of catheter insert elongated body 76 or may be covered by another material, such as a lubricious coating. In other examples, layer of second material 72 can be a middle layer of the wall of catheter insert elongated body 76, e.g., positioned between structural layers of silicone rubber or another suitable flexible material.

Layer of first material 74 and/or layer of second material 72 may be relatively non-permeable to substances of interest, such as oxygen and/or carbon dioxide. In some examples, layer of first material 74 and/or layer of second material 72 may be nylon, PET, or PTFE. In some examples layer of first material 74 and/or layer of second material 72 is relatively thin. For example, layer of first material 74 and/or layer of second material 72 layer of material 32 may be in the range of 0.001 to 0.100 inches (0.0254 mm to 2.54 mm). By keeping layer of first material 74 and/or layer of second material 72 relatively thin, catheter insert elongated body 76 may remain flexible. In some examples, layer of first material 74 and/or layer of second material 72 material 32 extend along an entire length of catheter insert elongated body 76 from a body distal end to a body proximal end, while in other examples, layer of first material 74 and/or layer of second material 72 only extend along part of a length of catheter insert elongated body 76.

In addition, in some examples, layer of first material 74 and/or layer of second material 72 extend around an entire perimeter of catheter insert elongated body 58, while in other examples, layer of first material 74 and/or layer of second material 72 extend around less than an entire perimeter of catheter insert elongated body 76, such as about 90% or more of the entire perimeter of catheter insert elongated body 76, which may help maintain a desired level of flexibility of catheter insert elongated body 76.

Figure 5:
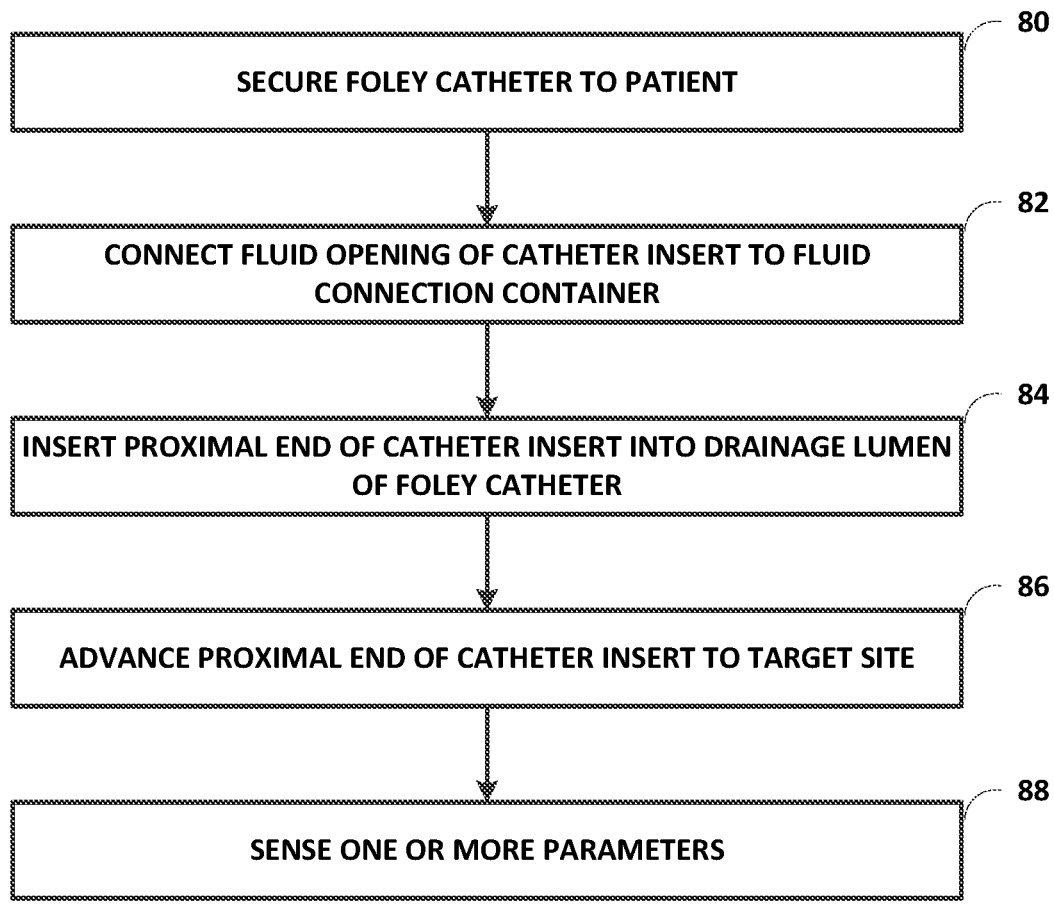
FIG. 5 is a flowchart illustrating an example method of operating a medical device.

FIG. 5 is a flowchart illustrating an example method of using Foley catheter 10 and catheter insert 50. A clinician may insert Foley catheter 10 into a patient's bladder and then secure, via an anchoring member on a proximal portion of the elongated body of the Foley catheter, the Foley catheter to a patient (80). For example, the clinician may secure Foley catheter 10, via anchoring member 18 to the patient. For example, the clinician may connect inflation opening 14B to an inflation device and inflate anchoring member 18, for example, using an inflation device and inflation fluid, such as sterile water, saline, or a gas. In examples in which anchoring member 18 is an expandable structure, the clinician may deploy anchoring member 18 by pushing a structure radially outwards or pulling back on a structure to cause the expandable structure to expand radially outwards.

The clinician may connect a fluid opening on the first distal end of a catheter insert 50 to a fluid collection container. For example, the clinician may connect second body fluid opening 56 of catheter insert 50 to a fluid collection container, such as a urine bag. The clinician may introduce a proximal end of catheter insert 50 into a drainage lumen of the Foley catheter, the catheter insert comprising a catheter insert elongated body defining a body lumen (84). For example, the clinician may insert body proximal end 62 of catheter insert 50 into lumen 34 of Foley catheter 10. The clinician may insert body proximal end 62 of catheter insert 50 into lumen 34 before inserting Foley catheter 10 into the patient's bladder or after Foley catheter 10 is positioned in the patient.

The clinician may advance body proximal end 62 of catheter insert 50 to a target site in the lumen 34 (86). For example, the clinician may advance body proximal end 62 of catheter insert 50 through the patient to a target site, such as proximal to anchoring member 18 of Foley catheter 10 and distal to proximal fluid opening 13.

One or more sensors positioned on the catheter insert elongated body may sense one or more parameters, at least one of the one or more parameters comprising a substance of interest in a fluid in the body lumen (88). For example, one or more sensors 52 may sense one or more parameters of urine being transported through body lumen 66. For example, one or more sensors 52 may physically contact urine flowing through body lumen 66 and may sense one or more parameters such as temperature, pressure, urine output (e.g., flow or volume), urine concentration, amount of dissolved oxygen in the urine, amount of dissolved carbon dioxide in the urine, urine pH, urine color, urine creatinine, and/or motion. In some examples, the substance of interest may be at least one of oxygen or carbon dioxide. In some examples, one or more sensors 52 may sense urine between catheter insert 50 and a fluid collection container.

While the example of FIG. 5, sets forth a number of steps, these steps may be performed in a different order or concurrently. For example, the clinician may connect the fluid opening 56 of catheter insert 50 to the fluid collection container after introducing body proximal end 62 of catheter insert 50 into lumen 34 of Foley catheter 10.

Figure 6:
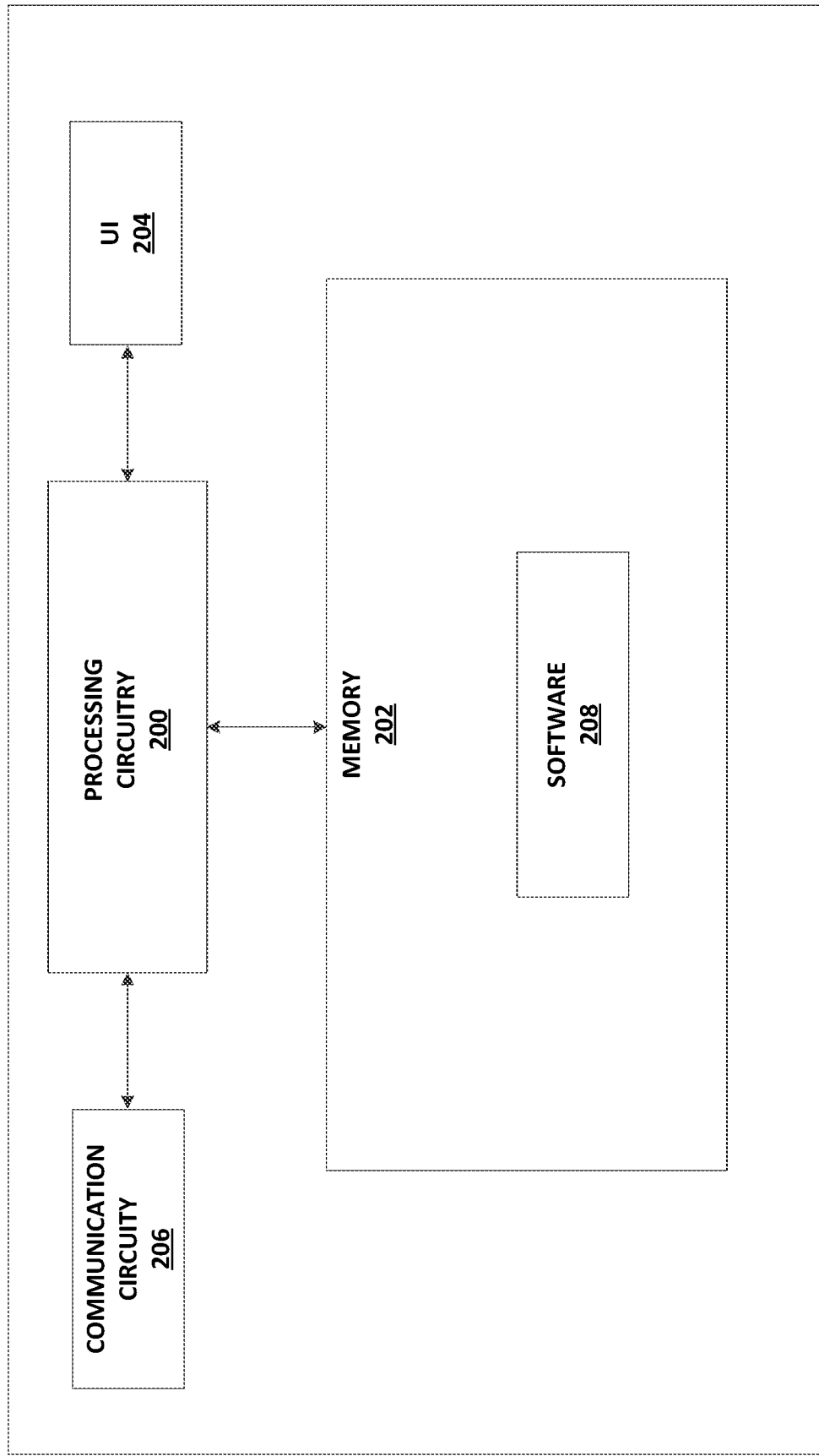
FIG. 6 is a block diagram of an example external device that may be used with a medical device.

FIG. 6 is a functional block diagram illustrating an example of an external device 24 configured to communicate with one or more sensors 52 of catheter insert 50 and receive information from one or more sensors 52. In the example of FIG. 6, external device 24 includes processing circuitry 200, memory 202, user interface (UI) 204, and communication circuitry 206. External device 24 may be a dedicated hardware device with dedicated software for the reading sensor data. Alternatively, external device 24 may be an off-the-shelf computing device, e.g., a desktop computer, a laptop computer, a tablet, or a smartphone running a mobile application that enables external device 24 to read sensor data from one or more sensors 52.

In some examples, a user of external device 24 may be clinician, physician, or heath care giver. In some examples, a user uses external device 24 to monitor a patient's kidney function. In some examples, the user may interact with external device 24 via UI 204, which may include a display to present a graphical user interface to the user, and a keypad or another mechanism (such as a touch sensitive screen) for receiving input from the user. External device 24 may communicate with one or more sensors 52 using wired, wireless or optical methods through communication circuitry 206.

Processing circuitry 200 may include any combination of integrated circuitry, discrete logic circuity, analog circuitry, such as one or more microprocessors, digital signal processors (DSPs), application specific integrated circuits (ASICs), or field-programmable gate arrays (FPGAs). In some examples, processing circuitry 200 may include multiple components, such as any combination of one or more microprocessors, one or more DSPs, one or more ASICs, or one or more FPGAs, as well as other discrete or integrated logic circuitry, and/or analog circuitry.

Memory 202 may store program instructions, such as software 208, which may include one or more program modules, which are executable by processing circuitry 200. When executed by processing circuitry 200, such program instructions may cause processing circuitry 200 and external device 24 to provide the functionality ascribed to them herein. The program instructions may be embodied in software and/or firmware. Memory 202 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

This disclosure includes the following examples.

Example 1. A device comprising: an elongated body defining a body lumen, the elongated body being configured to be at least partially proximally inserted into a catheter lumen defined by a catheter without covering a proximal fluid opening of the catheter and to form a fluidically tight coupling with the catheter; and one or more sensors positioned on the elongated body, at least one sensor of the one or more sensors configured to sense a substance of interest of a fluid within the body lumen, wherein the elongated body comprises a material that is a substantially non-permeable to the substance of interest.

Example 2. The device of example 1, wherein the one or more sensors comprises at least one of a temperature sensor, a pressure sensor, a dissolved gas sensor, a flow sensor, a volume sensor, a pH sensor, a creatinine sensor, a color sensor, urine electrical conductivity sensor, urine specific gravity sensor, urine biomarkers sensor, or a motion sensor.

Example 3. The device of example 1 or 2, wherein the one or more sensors comprise a dissolved gas sensor comprising at least one of a dissolved oxygen sensor or a dissolved carbon dioxide sensor.

Example 4. The device of any combination of examples 1-3, wherein the material is configured to minimize a flow of the substance of interest from the body lumen to an environment outside the elongated body.

Example 5. The device of any combination of examples 1-4, wherein the material comprises at least one of nylon, polyethylene terephthalate (PET), or polytetrafluoroethylene (PTFE).

Example 6. The device of any combination of examples 1-5, wherein the substance of interest comprises at least one of oxygen or carbon dioxide.

Example 7. The device of any combination of examples 1-6, wherein material is a first material and the elongated body comprises a layer of the first material and a layer of a second material permeable to the substance of interest.

Example 8. The device of example 7, wherein the first material is disposed on an inner surface of the elongated body, the inner surface defining the body lumen.

Example 9. The device of example 7 or 8, wherein the first material is disposed on an outer surface of the elongated body.

Example 10. The device of any combination of examples 1-9, wherein at least one sensor of the one or more sensors is positioned on a distal portion of the elongated body, the distal portion having a cross-sectional dimension larger than the catheter lumen to enable the distal portion to remain external to the catheter lumen when the elongated body is inserted into the catheter lumen.

Example 11. The device of example 10, wherein the distal portion defines a funnel.

Example 12. The device of example 10 or 11, wherein the distal portion is configured to connect to a fluid collection container.

Example 13. The device of any combination of examples 1-12, wherein the material extends from a first distal portion of the elongated body to a proximal portion of the elongated body and wherein the body lumen is configured to transport urine from the proximal portion to the distal portion.

Example 14. An assembly comprising: a Foley catheter comprising a catheter elongated body defining a drainage lumen, the catheter elongated body comprising a catheter distal portion and a catheter proximal portion, the catheter proximal portion defining a first drainage opening fluidically coupled to the drainage lumen and the catheter distal portion defining a second drainage opening fluidically coupled to the drainage lumen; and a catheter insert comprising: a catheter insert elongated body defining a body lumen, the catheter insert elongated body comprising a first body distal portion, a second body distal portion and a body proximal portion, the body proximal portion defining a first body fluid opening fluidically coupled to the body lumen and the first body distal portion defining a second body fluid opening fluidically coupled to the body lumen, wherein the catheter insert elongated body is configured such that when the first body distal portion is connected to the Foley catheter while the second body distal portion and the body proximal portion are inserted in the drainage lumen, a proximal end of the catheter insert elongated body remains distal to the first drainage opening of the Foley catheter; and one or more sensors positioned on the catheter insert elongated body, at least one of the one or more sensors configured to sense a substance of interest, wherein the catheter insert elongated body comprises a material that is a substantially non-permeable to the substance of interest, the material extending from the first body fluid opening to the at least one of the one or more sensors.

Example 15. The assembly of example 14, wherein at least one sensor of the one or more sensors is positioned on the first distal portion of the catheter insert elongated body.

Example 16. The assembly of example 15, wherein the at least one sensor comprises a dissolved gas sensor comprising at least one of a dissolved oxygen sensor or a dissolved carbon dioxide sensor.

Example 17. The assembly of any combination of examples 14-16, wherein the one or more sensors comprises at least one of a temperature sensor, a pressure sensor, a dissolved gas sensor, a flow sensor, a volume sensor, a pH sensor, a creatinine sensor, a color sensor, urine electrical conductivity sensor, urine specific gravity sensor, urine biomarkers sensor, or a motion sensor.

Example 18. The assembly of any combination of examples 14-17, wherein the material comprises at least one of nylon, polyethylene terephthalate (PET), or polytetrafluoroethylene (PTFE), and the catheter insert is stiffer than the Foley catheter.

Example 19. The assembly of any combination of examples 14-18, wherein the catheter insert is configured to form a fluid tight coupling with the Foley catheter.

Example 20. A method comprising: introducing a proximal end of a catheter insert into a lumen of a catheter, the catheter insert comprising: an elongated body defining a body lumen; and one or more sensors positioned on the elongated body, at least one sensor of the one or more sensors configured to sense a substance of interest of a fluid within the body lumen, wherein the elongated body comprises a material that is a substantially non-permeable to the substance of interest; proximally advancing the catheter insert into the drainage lumen so that a proximal end of the catheter insert is proximal to an anchoring member of the catheter and distal to a proximal fluid opening of the catheter; and fluidically coupling the catheter insert and the catheter.

Example 21. The method of example 20, wherein the one or more sensors comprise at least one of a temperature, pressure, a dissolved gas sensor, a flow sensor, a volume sensor, a pH sensor, a creatinine sensor, a color sensor, urine electrical conductivity sensor, urine specific gravity sensor, urine biomarkers sensor, or a motion sensor.

Example 22. The method of example 20 or 21, wherein the one or more sensors comprise a dissolved gas sensor comprising at least one of a dissolved oxygen sensor or a dissolved carbon dioxide sensor.

Example 23. The method of any combination of examples 20-22, wherein the material is configured to minimize a flow of the substance of interest from the body lumen to an environment outside the catheter insert elongated body.

Example 24. The method of any combination of examples 20-23, wherein the material comprises at least one of nylon, polyethylene terephthalate (PET), or polytetrafluoroethylene (PTFE).

Example 25. The method of any combination of examples 20-24, wherein the substance of interest comprises at least one of oxygen or carbon dioxide.

Example 26. The method of any combination of examples 20-25, wherein the material is a first material and the catheter insert elongated body comprises a layer of the first material and a layer of a second material permeable to the substance of interest.

Example 27. The method of example 26, wherein the first material is disposed on an inner surface of the catheter insert elongated body, the inner surface defining the body lumen.

Example 28. The method of example 26 or 27, wherein the first material is disposed on an outer surface of the catheter insert elongated body.

Example 29. The method of any combination of examples 20-28, further comprising: connecting a fluid opening on a distal end of the catheter insert to a fluid collection container.

Various examples have been described. These and other examples are within the scope of the following claims.

What is claimed is:

1. An assembly comprising:
   a Foley catheter comprising a catheter elongated body defining a drainage lumen, the catheter elongated body comprising a catheter distal portion and a catheter proximal portion, the catheter proximal portion defining a first drainage opening fluidically coupled to the drainage lumen and the catheter distal portion defining a second drainage opening fluidically coupled to the drainage lumen; and
   a catheter insert configured to be at least partially inserted into the drainage lumen and configured to be removeable from the drainage lumen, the catheter insert comprising:
      a catheter insert elongated body defining a body lumen, the catheter insert elongated body comprising a first body distal portion, a second body distal portion and a body proximal portion, the body proximal portion defining a first body fluid opening fluidically coupled to the body lumen and the first body distal portion defining a second body fluid opening fluidically coupled to the body lumen, wherein the catheter insert elongated body is configured such that while the second body distal portion and the body proximal portion are inserted in the drainage lumen, a proximal end of the catheter insert elongated body remains distal to the first drainage opening of the Foley catheter; and
      one or more sensors positioned on the catheter insert elongated body, at least one of the one or more sensors configured to sense a substance of interest, wherein the catheter insert elongated body comprises a material that is a substantially non-permeable to the substance of interest, the material extending from the first body fluid opening to the at least one of the one or more sensors.

2. The assembly of claim 1, wherein at least one sensor of the one or more sensors is positioned on the first distal portion of the catheter insert elongated body.

3. The assembly of claim 2, wherein the at least one sensor comprises a dissolved gas sensor comprising at least one of a dissolved oxygen sensor or a dissolved carbon dioxide sensor.

4. The assembly of claim 1, wherein material is a first material and the elongated body comprises a layer of the first material and a layer of a second material permeable to the substance of interest.

5. The assembly of claim 4, wherein the first material is disposed on an outer surface of the catheter insert elongated body.

6. The assembly of claim 1, wherein the at least one sensor is positioned on the first body distal portion, the first body distal portion having a cross-sectional dimension larger than the drainage lumen to enable the first body distal portion to remain external to the drainage lumen when the catheter insert elongated body is inserted into the drainage lumen.

7. The assembly of claim 6, wherein the first body distal portion defines a funnel.

8. The assembly of claim 1, wherein the one or more sensors comprises at least one of a temperature sensor, a pressure sensor, a dissolved gas sensor, a flow sensor, a volume sensor, a pH sensor, a creatinine sensor, a color sensor, urine electrical conductivity sensor, urine specific gravity sensor, urine biomarkers sensor, or a motion sensor.

9. The assembly of claim 1, wherein the material comprises at least one of nylon, polyethylene terephthalate (PET), or polytetrafluoroethylene (PTFE), and the catheter insert is stiffer than the Foley catheter.

10. The assembly of claim 1, wherein the catheter insert is configured to form a fluid tight coupling with the Foley catheter.

11. The assembly of claim 1, wherein the substance of interest comprises at least one of oxygen or carbon dioxide.

12. The assembly of claim 4, wherein the first material is disposed on an inner surface of the catheter insert elongated body, the inner surface defining the body lumen.

13. The assembly of claim 1, wherein the first body distal portion is configured to connect to a fluid collection canister.

14. The assembly of claim 1, wherein the material extends from the first body distal portion to the body proximal portion, and wherein the body lumen is configured to transport urine from the body proximal portion to the first body distal portion.

15. A method comprising:
   at least partially inserting a catheter insert into a drainage lumen of a Foley catheter, the catheter insert being removeable from the drainage lumen, wherein the Foley catheter comprises a catheter elongated body defining the drainage lumen, the catheter elongated body comprising a catheter distal portion and a catheter proximal portion, the catheter proximal portion defining a first drainage opening fluidically coupled to the drainage lumen and the catheter distal portion defining a second drainage opening fluidically coupled to the drainage lumen; and wherein the catheter insert comprises:
      an elongated body defining a body lumen, the catheter insert elongated body comprising a first body distal portion, a second body distal portion and a body proximal portion, the body proximal portion defining a first body fluid opening fluidically coupled to the body lumen and the first body distal portion defining a second body fluid opening fluidically coupled to the body lumen, wherein the catheter insert elongated body is configured such that while the second body distal portion and the body proximal portion are inserted in the drainage lumen, a proximal end of the catheter insert elongated body remains distal to the first drainage opening of the Foley catheter; and
      one or more sensors positioned on the catheter insert elongated body, at least one sensor of the one or more sensors configured to sense a substance of interest of a fluid within the body lumen,
      wherein the catheter insert elongated body comprises a material that is a substantially non-permeable to the substance of interest, wherein the catheter insert elongated body comprises a material that is a substantially non-permeable to the substance of interest, the material extending from the first body fluid opening to the at least one of the one or more sensors;
   proximally advancing the catheter insert into the drainage lumen so that a proximal end of the catheter insert is proximal to an anchoring member of the catheter and distal to a proximal fluid opening of the catheter; and fluidically coupling the catheter insert and the catheter.

16. The method of claim 15, wherein the one or more sensors comprise at least one of a temperature, pressure, a dissolved gas sensor, a flow sensor, a volume sensor, a pH sensor, a creatinine sensor, a color sensor, urine electrical conductivity sensor, urine specific gravity sensor, urine biomarkers sensor, or a motion sensor.

17. The method of claim 15, wherein the one or more sensors comprise a dissolved gas sensor comprising at least one of a dissolved oxygen sensor or a dissolved carbon dioxide sensor.

18. The method of claim 15, wherein the material is configured to minimize a flow of the substance of interest from the body lumen to an environment outside the catheter insert elongated body.

19. The method of claim 15, wherein the material comprises at least one of nylon, polyethylene terephthalate (PET), or polytetrafluoroethylene (PTFE).

20. The method of claim 15, wherein the substance of interest comprises at least one of oxygen or carbon dioxide.

21. The method of claim 15, further comprising:

connecting a fluid opening on a distal end of the catheter insert to a fluid collection container.

* * * * *